United States Patent [19]

Hartung

[11] 4,176,228
[45] Nov. 27, 1979

[54] POTASSIUM-MAGNESIUM-CALCIUM GLYCYRRHIZIN

[75] Inventor: Harold A. Hartung, West Collingswood, N.J.

[73] Assignee: MacAndrews and Forbes Company, Camden, N.J.

[21] Appl. No.: 942,313

[22] Filed: Sep. 14, 1978

[51] Int. Cl.² ............................................. C07H 15/20
[52] U.S. Cl. ........................................ 536/4; 426/658; 536/121
[58] Field of Search .............................................. 536/4

[56] References Cited

U.S. PATENT DOCUMENTS

| | | | |
|---|---|---|---|
| 3,046,195 | 7/1962 | Zagt, Jr. ................................ | 536/4 |
| 3,066,072 | 11/1962 | Gottfried et al. ........................ | 536/4 |
| 3,164,581 | 1/1965 | Muravjev et al. ....................... | 536/4 |
| 3,282,706 | 11/1966 | Muller et al. ............................ | 536/4 |
| 3,379,717 | 4/1968 | Koopman et al. ....................... | 536/4 |
| 3,629,231 | 12/1971 | Hough et al. ............................ | 536/4 |
| 3,812,097 | 5/1974 | Baran et al. ............................. | 536/4 |
| 3,940,381 | 2/1976 | Boissevain .............................. | 536/4 |

Primary Examiner—Johnnie R. Brown
Attorney, Agent, or Firm—Howson and Howson

[57] ABSTRACT

A flavoring or sweetening agent comprising potassium-magnesium-calcium glycyrrhizin of the formula $K_xMg_yCa_zG$ wherein G is glycyrrhizic acid and the sum of x, 2y and 2z is 2 and a process for recovering this product from licorice root are disclosed.

9 Claims, No Drawings

POTASSIUM-MAGNESIUM-CALCIUM GLYCYRRHIZIN

BACKGROUND OF THE INVENTION

Licorice root, a complex product of nature and the only botanical known to contain appreciable levels of glycyrrhizin, has been subjected to many different procedures in efforts to realize the maximum yield of useful products from the root. Glycyrrhizin, one of the principal active ingredients in licorice root, is present in root at concentrations ranging from 2 to 15 percent. Techniques for extraction of active components from the root generally include initial comminution of the root and extraction with hot water and steam. In the past, a variety of agents have been used in an attempt to increase the yield of glycyrrhizin obtained from fresh licorice root. Typical of such efforts are the procedures described in U.S. Pat. Nos. 762,032; 1,389,663; 1,849,569; and 2,058,019 and British Specification No. 988. For the most part, the enumerated references describe procedures which rely on the addition of alkali, acid or both and/or other chemical agents to hot water and/or steam to increase the yield of glycyrrhizin from fresh root. Copending U.S. Patent Application Ser. No. 764,896, filed Feb. 2, 1977, and assigned to the assignee of the present application, describes certain glycyrrhizin-free fractions of licorice root and a process for obtaining those fractions from "spent" licorice root.

The primary water soluble extract obtained from licorice root is a natural flavor which is widely used; it is a product containing glycyrrhizin and many other water soluble components. Customary practice involves further treatment of the primary extract to obtain more highly refined and purified products. Commercial root processors typically treat primary extract with acid causing precipitation to occur, and isolate the acid insoluble fraction which is known in the industry as crude glycyrrhizic acid.

Crude glycyrrhizic acid is customarily treated with ammonia to render it soluble, forming ammoniated glycyrrhizin, a product of intense sweetness which possesses the characteristic licorice flavor, albeit at reduced intensity. Monoammoniated glycyrrhizin, a more highly refined ammoniated glycyrrhizin, has found utility for its sweet flavor, and very recently the interest in the sweetening and flavoring properties of monoammoniated glycyrrhizin, and other products of licorice root origin, has heightened as widely used synthetic sweeteners are criticized and removed from the market place by government edict.

Those searching for an ideal low calorie sweetener are not necessarily faddists, but they cannot help but be influenced by the current enthusiasm shown for all "natural" products. Ammoniated glycyrrhizin is recognized as a natural product, and it is presently on the FDA list of natural flavoring agents generally recognized as safe. Food processors, however, have been somewhat reluctant to accord this product complete acceptance.

Among the factors which mitigate against widespread acceptance of ammoniated glycyrrhizin and monoammoniated glycyrrhizin as products suitable for universal adoption as flavoring and sweetening agents include the fact that ammoniated glycyrrhizin and to a lesser degree monoammoniated glycyrrhizin, possess characteristic licorice flavor and thus, need to be used in low concentrations where that flavor is undesirable. Furthermore, ammoniated glycyrrhizin has limited sweetness value in comparison with saccharin, a factor which would seemingly call for higher concentrations of the product than is required when saccharin is used as a sweetening agent. There also appears to be some apprehension in the food industry that the "natural" status which ammoniated glycyrrhizin and monoammoniated glycyrrhizin currently enjoy may be questioned ultimately in view of their ammonia content. Ammoniated glycyrrhizin has been criticized by some as imparting an "ammonia" taste to food products; it has also been found that when raw products containing ammoniated glycyrrhizin are baked, ammonia gas may be liberated, and this is not desired. In addition, monoammoniated glycyrrhizin has limited solubility in water, only 1 to 2%, by weight, being soluble in hot water. At concentrations beyond this, monoammoniated glycyrrhizin forms a gel in aqueous solutions.

Monoammoniated glycyrrhizin and ammoniated glycyrrhizin base products such as those described in U.S. Pat. No. 3,851,073 enjoy considerable commercial acceptance, a fact which indicates that licorice root must be given further careful consideration as a source for low calorie sweeteners and natural flavors, despite their enumerated shortcomings. Therefore, it is an object of this invention to overcome the shortcomings associated with ammoniated glycyrrhizin and monoammoniated glycyrrhizin by providing potassium-magnesium-calcium glycyrrhizin in a form analogous to that in which glycyrrhizin exists in licorice root prior to aqueous extraction.

DETAILED DESCRIPTION OF THE INVENTION

According to this invention, there is provided a potassium-magnesium-calcium glycyrrhizin of the formula $K_xMg_yCa_zG$ where G is glycyrrhizic acid and the sum of x, $2_y$ and $2_z$ is 2, and a process for recovering this product from licorice root.

As mentioned previously, glycyrrhizin exists in licorice root as part of a host of compounds, useful and non-useful, identified and non-identified, which make up the root. Those with experience in licorice root processing have determined that glycyrrhizin exists in licorice root in the form of mixed potassium-magnesium-calcium salts. The precise ratio of potassium, magnesium and calcium in the glycyrrhizin salts is found to vary with differing species of root and between samples of like root specie depending on the locale from which the root is obtained. Extracts from a variety of licorice root from many parts of the world have been analyzed to determine the content of potassium, magnesium and calcium in the root. It was found that despite the wide variety of sources, climate and soil conditions in which the root grew, that the proportion of potassium, magnesium and calcium in the root samples was relatively constant within the range $K_{0.51-0.71}Mg_{0.43-0.53}Ca_{0.18-0.22}G$, the average for all samples studied being $K_{0.6}Mg_{0.5}Ca_{0.2}G$. At the present time, it is not possible to commercially isolate or extract pure glycyrrhizin directly from licorice root in the form of its potassium-magnesium-calcium salts, although it would be desirable to do so in an effort to avoid the shortcomings associated with use of ammoniated glycyrrhizin and monoammoniated glycyrrhizin.

One aspect of this invention provides a process for recovery of potassium-magnesium-calcium glycyrrhizin of the formula $K_xMg_yCa_zG$ wherein G is glycyrrhizic acid and the sum of x, 2y and 2z is 2 from licorice root which comprises:

(a) extracting coarse ground licorice root with water at a temperature in excess of 20° C. producing an aqueous extract of the water soluble components of the root and an insoluble residue;

(b) separating and isolating said aqueous extract and said insoluble residue;

(c) treating the aqueous extract with sufficient acid to acidify the extract to a pH of from about 1 to 2.5, forming an acid soluble fraction and an acid insoluble precipitate of crude glycyrrhizic acid;

(d) separating and isolating said acid soluble fraction and said crude glycyrrhizic acid, (e) treating the glycyrrhizic acid with a mixture of alkali having potassium, magnesium and calcium cations in an amount sufficient to solubilize and alkalify the glycyrrhizic acid to a pH of from about 5 to about 6.5, said alkali mixture having potassium, magnesium and calcium cations present in a ratio one to the other sufficient that said alkalified glycyrrhizic acid comprises potassium-magnesium-calcium glycyrrhizin of the formula $K_xMg_yCa_zG$ wherein G is glycyrrhizic acid and the sum of x, 2y and 2z is 2, and recovering said potassium-magnesium-calcium glycyrrhizin solution.

Considered in greater detail, the process of this invention comprises extracting comminuted licorice root with water or steam at a temperature of from about 20° C. to about 150° C. Pressures above atmospheric may be used to faciliate the extraction process. Aqueous extraction results in rather complete solution of the glycyrrhizin content of licorice root. However, other water soluble components in the root are recovered in aqueous extraction so that the aqueous extract actually is a complex solution of glycyrrhizin and other soluble components. Licorice root extract has great buffering capacity, and, for this reason, the primary water soluble extracts recovered on extraction of fresh root will have a pH between about 5 and about 6, even though unbuffered aqueous extractants having a pH in the range of 3 to 12 are used in the extraction process.

After aqueous extraction is complete, an aqueous extract having a pH between 5 and 6 is isolated, and treated with sufficient acid to acidify the extract to a pH of from about 1 to about 2.5 forming an acid soluble fraction and an acid insoluble residue. Acidification serves to concentrate and purify the glycyrrhizin content of the aqueous extract in that glycyrrhizin is converted to glycyrrhizic acid which precipitates from the acidic solution leaving acid soluble components initially extracted from the root, in solution.

No special conditions are required for acidification of the alkaline extract, although it is preferred that acidification be carried out at temperatures from about 25° C. to about 45° C. Acids useful in the acidification of the aqueous extract include mineral acids such as sulfuric, hydrochloric and phosphoric acids, and a large number of organic acids which are sufficiently soluble and possess an ionization constant sufficiently high to provide the required hydrogen ion concentration. Organic acids, including but not limited to, acetic, butyric, citric, fumaric, glycolic, lactic, malic, oxalic, propionic, succinic, tartaric and vinylacetic acids may be used.

The acid insoluble crude glycyrrhizic acid is next treated with sufficient alkali to solubilize and alkalify the glycyrrhizic acid to a pH of from about 5 to 6.5, preferably about 6. The alkali used must contain a mixture of potassium, magnesium and calcium cations in a total amount sufficient to solubilize and alkalify the glycyrrhizic acid, the potassium, magnesium and calcium cations being present in a ratio one to the other sufficient that the alkalified glycyrrhizic acid comprises potassium-magnesium-calcium glycyrrhizin of the formula $K_xMg_yCa_zG$ wherein G is glycyrrhizic acid and the sum of x, $2_y$ and $2_z$ is 2. The crude glycyrrhizic acid may be purified by means known to those skilled in the art prior to the alkali treatment. For example, the crude glycyrrhizic acid may be purified to remove resinous materials which are insoluble in acid by treatment with solvents in which the glycyrrhizic acid is preferentially soluble and in which the resinous materials are insoluble. The preferential solution, involving precise pH control, results in concentration of the glycyrrhizic acid and removal of root-origin resinous materials which impart undesirable tan to brown color characteristics to crude glycyrrhizic acid.

No special conditions are required for the alkalification of glycyrrhizic acid, although it is preferred that the alkalification be carried out at temperatures of from about 25° C. to about 95° C. Alkalies useful in the alkalification of glycyrrhizic acid according to this invention must contain a mixture of potassium, magnesium and calcium cations, the alkali form is not critical, and may include oxide, hydroxide or bicarbonate, or mixtures of one or more of such forms, the hydroxide form being preferred. The potassium, magnesium and calcium cations in the alkali mixture are present in a ratio one to another sufficient that the potassium-magnesium-calcium glycyrrhizin produced has the formula $K_xMg_yCa_zG$, and the sum of x, $2_y$ and $2_z$ is 2. Typical products produced include those where x has a value of 0.51 to 0.71, y has a value of 0.43 to 0.53 and z has a value of 0.18 to 0.22, respectively.

The potassium-magnesium-calcium glycyrrhizin is recovered in solution form and may be used in that form, or, if desired, may be concentrated or dried by spray dying. Potassium-magnesium-calcium glycyrrhizin of this invention has properties and characteristics as a sweetener and flavoring agent which are distinctly different from those of other products derived from licorice root according to technology available in the art today. For example, potassium-magnesium-calcium glycyrrhizin is highly soluble, being soluble more than 35%, by weight, in water. Thus, it can be spray dried efficiently, and in this form it can be packaged, stored, shipped and used with great convenience. An interesting observation which demonstrates the unique and novel properties of the new glycyrrhizin salt is the fact neight calcium hydroxide nor magnesium hydroxide are water soluble, yet when these alkalies are combined with potassium hydroxide in the ratio described herein and the mixture of these alkalies is used in the process described herein, the potassium-magnesium-calcium glycyrrhizin obtained is highly soluble in water. Potassium-magnesium-calcium glycyrrhizin produced in this invention is a pure derivative of licorice root; it has sweetness and flavor characteristics comparable to that of ammoniated glycyrrhizin or monoammoniated glycyrrhizin, yet is free of the shortcomings associated with those products, e.g. low solubility in water, ammonia taste, gas production and the like. Significant too, is the fact that the glycyrrhizin salt of this invention is combined with the metal cations glycyrrhizin is associated with in licorice root, and that, heretofore, it has not been possible to extract or isolate glycyrrhizin from natural root in association with potassium, magnesium and calcium metal cations.

Since the potassium-magnesium-calcium glycyrrhizin salt of this invention is derived from licorice root, it, like licorice extract, glycyrrhiza, and ammoniated glycyrrhizin, should be categorized by the FDA as generally recognized as safe (GRAS). To this end, the alkali and acids used in producing the product should conform to the standards of the *Food Chemical Codex.*

The complete scope of utility of potassium-magnesium-calcium glycyrrhizin as a natural sweetener and flavor adjunct has not been determined. In general, however, an acceptable sweetening effect can be achieved with as little as 0.01% or as much as 5%, preferably about 0.1 to 0.5%, by weight, based on the weight of the product, of the glycyrrhizin salt.

The following example illustrates preparation and utility of potassium-magnesium-calcium glycyrrhizin salts.

EXAMPLE 1

2000 g. coarse ground licorice root was extracted with 10,000 ml. of water at 60° C., and 6200 ml. (1) of aqueous extract was recovered. 45 g. $H_2SO_4$ was added to the aqueous extract forming an acid soluble fraction having a pH of 1.8 and an acid insoluble precipitate of glycyrrhizic acid. 115 g. of glycyrrhizic acid (dry basis) was added slowly with stirring to 200 ml. water containing 5 g. potassium hydroxide, 4 g. magnesium hydroxide and 2 g. calcium hydroxide. The glycyrrhizic acid was solubilized forming a concentrated solution of $K_{0.6}Mg_{0.5}Ca_{0.2}$ glycyrrhizinate having a pH of 6. When evaluated by a flavor panel, this product was found to be sweeter and was preferred as a flavoring material over ammoniated glycyrrhizin. The product was highly water soluble.

EXAMPLE 2

Glycyrrhizic acid prepared from licorice root in the manner described in Example 1, was converted to ammoniated glycyrrhizin by treatment with aqua ammonia; the solution was spray dried and 115 g. of the ammoniated glycyrrhizin was slowly added with vigorous stirring to 200 ml. of water heated to a temperature of 90° C. containing 5 g. potassium hydroxide, 4 g. magnesium hydroxide and 2 g. calcium hydroxide. The glycyrrhizic acid formed by displacing the ammonia was completely solubilized forming a concentrated solution of $K_{0.6}Mg_{0.5}Ca_{0.2}$ glycyrrhizinate having a pH of 6. When evaluated by flavor panel, the product was found to be sweeter, and was preferred as a flavoring material, over ammoniated glycyrrhizin.

EXAMPLE 3

Glycyrrhizic acid prepared from licorice root in the manner described in Example 1, was purified and converted into monoammoniated glycyrrhizin and 115 g. of the monoammoniated glycyrrhizin was slowly added with vigorous stirring to 200 ml. of water at 90° C. containing 5 g. potassium hydroxide, 4 g. magnesium hydroxide and 2 g. calcium hydroxide. The glycyrrhizic acid formed by displacing the ammonia was completely solubilized forming a concentrated solution of $K_{0.6}Mg_{0.5}Ca_{0.2}$ glycyrrhizinate having a pH of 6. When evaluated by flavor panel, this product was found to be sweeter, and was preferred as a flavoring material, over ammoniated glycyrrhizin.

What is claimed is:

1. A process for recovery of potassium-magnesium-calcium glycyrrhizin of the formula $K_xMg_yCa_zG$ where G is glycyrrhizic acid and the sum of x, 2y and 2z is 2 from licorice root which comprises:
    (a) extracting coarse ground licorice root with water at a temperature in excess of 20° C. and not greater than about 150° C. producing an aqueous extract of the water soluble components of the root and an insoluble residue;
    (b) separating and isolating said aqueous extract and said insoluble residue;
    (c) treating the aqueous extract with sufficient acid to acidify the extract to a pH of from about 1 to about 2.5, forming an acid soluble fraction and an acid insoluble precipitate of glycyrrhizic acid;
    (d) separating and isolating said acid soluble fraction and said glycyrrhizic acid;
    (e) treating the glycyrrhizic acid with a mixture of alkali having potassium, magnesium and calcium cations in an amount sufficient to solubilize and alkalify the glycyrrhizic acid to a pH of from 5 to 6.5, said alkali mixture having potassium, magnesium and calcium cations present in a ratio one to the other sufficient that said alkalified glycyrrhizic acid comprises potassium-magnesium-calcium glycyrrhizin of the formula $K_xMg_yCa_zG$ wherein G is glycyrrhizic acid and the sum of x, 2y and 2z is 2, and
    (f) recovering said potassium-magnesium-calcium glycyrrhizin solution.

2. The process of claim 1 wherein the glycyrrhizic acid is treated with alkali selected from the group consisting of potassium hydroxide, magnesium hydroxide and calcium hydroxide.

3. The process of claim 1 wherein said potassium-magnesium-calcium glycyrrhizin has the formula $K_{0.51-0.71}Mg_{0.43-0.53}Ca_{0.18-0.22}G$.

4. The process of claim 3 wherein said potassium-magnesium calcium glycyrrhizin has the formula $K_{0.6}Mg_{0.5}Ca_{0.2}G$.

5. The process of claim 1 wherein the glycyrrhizic acid isolated in step (d) is treated with aqua ammonia to convert said acid to ammoniated glycyrrhizin, and said ammoniated glycyrrhizin is treated with a mixture of alkali having potassium, magnesium and calcium cations in an amount sufficient to solubilize and alkalify the ammoniated glycyrrhizin forming a concentrated solution of $K_{0.6}Mg_{0.5}Ca_{0.2}$ glycyrrhizinate having a pH of 6.

6. The process of claim 1 wherein the glycyrrhizic acid isolated in step (d) is treated with aqua ammonia to convert said acid to monoammoniated glycyrrhizin, and said ammoniated glycyrrhizin is treated with a mixture of alkali having potassium, magnesium and calcium cations in an amount sufficient to solubilize and alkalify the ammoniated glycyrrhizin forming a concentrated solution of $K_{0.6}Mg_{0.5}Ca_{0.2}$ glycyrrhizinate having a pH of 6.

7. Potassium-magnesium-calcium glycyrrhizin of the formula $K_xMg_yCa_zG$ wherein G is glycyrrhizic acid and the sum of x, 2y and 2z is 2.

8. Potassium-magnesium-calcium glycyrrhizin of claim 7 having the formula $K_{0.51-0.71}Mg_{0.43-0.53}Ca_{0.18-0.22}G$.

9. Potassium-magnesium-calcium glycyrrhizin of claim 7 having the formula $K_{0.6}Mg_{0.5}Ca_{0.2}G$.

* * * * *